(12) United States Patent
Castiglione (10) Patent No.: US 12,017,095 B2
(45) Date of Patent: Jun. 25, 2024

(54) RESPIRATOR CONFIGURED TO ACCEPT VISION-PROTECTING MODULE

(71) Applicant: 3M INNOVATIVE PROPERTIES COMPANY, St. Paul, MN (US)

(72) Inventor: David M. Castiglione, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 743 days.

(21) Appl. No.: 16/972,866

(22) PCT Filed: May 31, 2019

(86) PCT No.: PCT/IB2019/054542
§ 371 (c)(1),
(2) Date: Dec. 7, 2020

(87) PCT Pub. No.: WO2019/234572
PCT Pub. Date: Dec. 12, 2019

(65) Prior Publication Data
US 2021/0244976 A1      Aug. 12, 2021

Related U.S. Application Data

(60) Provisional application No. 62/681,988, filed on Jun. 7, 2018.

(51) Int. Cl.
*A62B 18/08*     (2006.01)
*A62B 18/02*     (2006.01)

(52) U.S. Cl.
CPC ............ *A62B 18/082* (2013.01); *A62B 18/02* (2013.01); *A62B 18/084* (2013.01)

(58) Field of Classification Search
CPC . A62B 18/00; A62B 18/02; A62B 18/08–084; A62B 7/00; A62B 7/10; A62B 9/00; A62B 9/04; A62B 23/00–02; A61F 9/022–023; A61F 9/06–067
See application file for complete search history.

(56) References Cited

U.S. PATENT DOCUMENTS

| 3,147,487 A | 9/1964 | Hoeftman |
| 3,276,034 A | 10/1966 | Cupp |
| 4,069,516 A * | 1/1978 | Watkins, Jr. ........... A62B 18/08 2/428 |
| 4,648,394 A | 3/1987 | Wise |

(Continued)

FOREIGN PATENT DOCUMENTS

| KR | 2019890001128 | 3/1989 |
| KR | 101700604 | 1/2017 |

(Continued)

OTHER PUBLICATIONS

"3M™ Clip-on Welding Shield Kit 7990/7990-AM and Electronic Lens Assembly 7991/7991-AM", Literature, 2004, pp. 1-2.

(Continued)

*Primary Examiner* — Rachel T Sippel
(74) *Attorney, Agent, or Firm* — Kenneth B. Wood (57) ABSTRACT

A respirator including a facepiece with a transparent lens that is recessed radially-inwardly relative to an opaque frame of an opaque chassis of the facepiece. The respirator is configured to receive a vision-protecting module.

10 Claims, 8 Drawing Sheets

(56) References Cited

U.S. PATENT DOCUMENTS

| | | |
|---|---|---|
| 6,176,239 B1 | 1/2001 | Grove |
| 6,185,739 B1 | 2/2001 | Verkic |
| 7,523,755 B2 | 4/2009 | Richardson |
| 7,594,510 B2 | 9/2009 | Betz |
| 8,113,200 B2 | 2/2012 | Davis |
| 8,839,788 B2 | 9/2014 | Betz |
| 8,873,170 B2 | 10/2014 | Patil |
| 9,861,529 B2 | 1/2018 | Seo |
| 2007/0235031 A1 | 10/2007 | Betz |
| 2010/0065058 A1* | 3/2010 | Ungar .................... A62B 18/02 128/206.24 |
| 2011/0100370 A1* | 5/2011 | Rose .................... A62B 18/084 264/271.1 |
| 2016/0074230 A1 | 3/2016 | Sernfält |
| 2016/0081856 A1* | 3/2016 | Hofer-Kraner ......... A61F 9/067 2/8.3 |
| 2019/0235623 A1* | 8/2019 | Pollard .................... G02B 7/09 |

FOREIGN PATENT DOCUMENTS

| | | |
|---|---|---|
| WO | WO1992-020405 | 11/1992 |
| WO | WO 2012/009659 | 1/2012 |
| WO | WO2014-081209 | 5/2014 |

OTHER PUBLICATIONS

"3M™ Full Face Mask FF-400 Series", Technical Datasheet, 2012, pp. 1-7.
"3M™ Full Facepiece Respirator 6000 Sales", Literature, 2005, pp. 1-2.
International Search Report for PCT International Application No. PCT/IB2019/054542, mailed on Oct. 17, 2019, 3 pages.

* cited by examiner

RESPIRATOR CONFIGURED TO ACCEPT VISION-PROTECTING MODULE

CROSS REFERENCE TO RELATED APPLICATIONS

This application is a national stage filing under 35 U.S.C. 371 of PCT/IB2019/054542, filed May 31, 2019, which claims the benefit of provisional Application No. 62/681,988, filed Jun. 7, 2018, the disclosure of which is incorporated by reference in its/their entirety herein.

BACKGROUND

Respirators for providing a breathable air supply to a wearer are used in a variety of applications. The respirators can be used during fires, military operations and hazardous industrial operations where the air supply may be contaminated. In addition to providing a clean air source to the nose and mouth for breathing, full-face respirators also protect the eyes and face from harmful or irritating gases and other substances. The devices can further include mounts for accepting detachable and replaceable filter elements or connectors to air supplies.

SUMMARY

In broad summary, herein is disclosed a respirator comprising a facepiece with a transparent lens that is recessed radially-inwardly relative to an opaque frame of an opaque chassis of the facepiece. respirator is configured to receive a vision-protecting module. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated.

The term "respirator" signifies a personal respiratory protection device that is worn by a person to filter air before the air enters the person's respiratory system. A "full-face" respirator is one that is worn over the person's nose, mouth and eyes.

Figure 5:
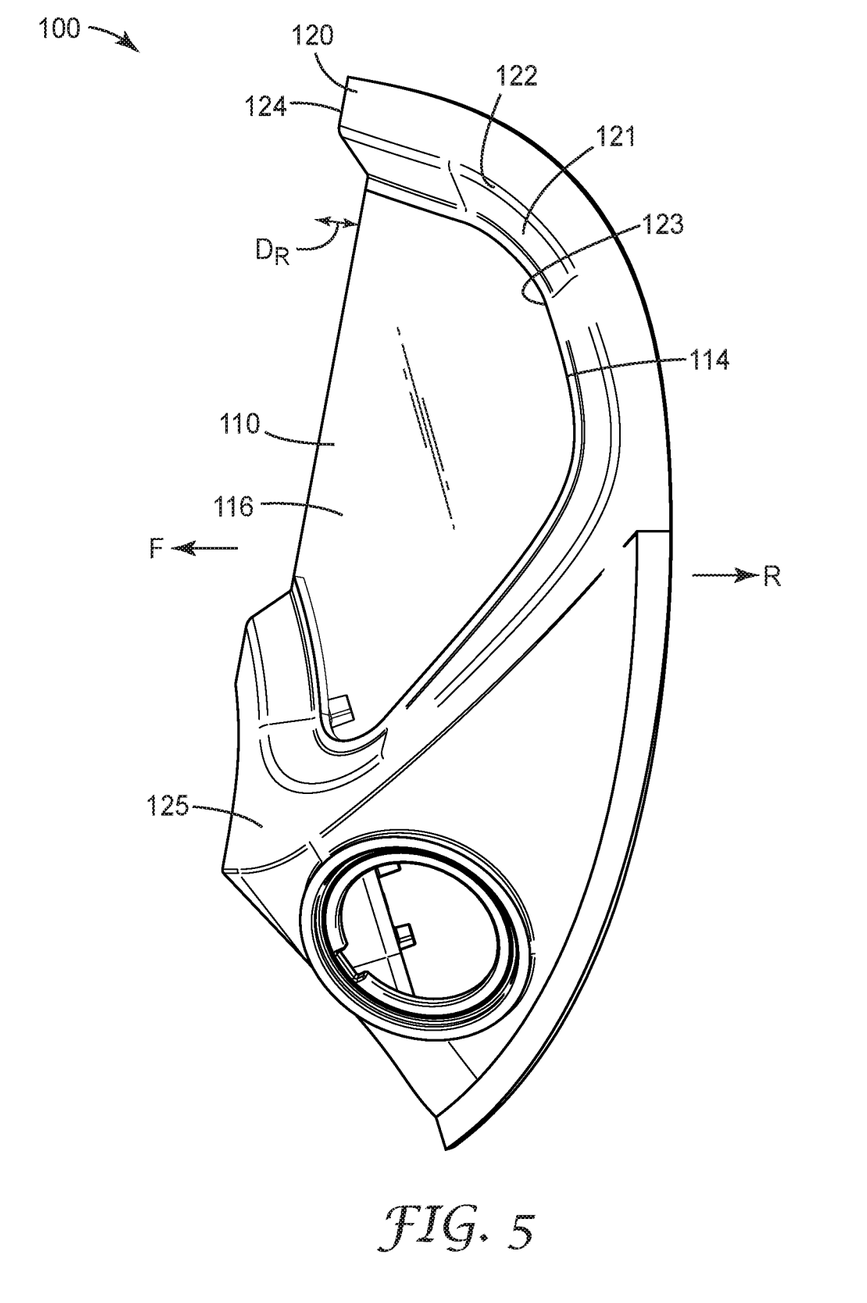
FIG. 5 is a side view of the exemplary facepiece of FIG. 4.
Figure 6:
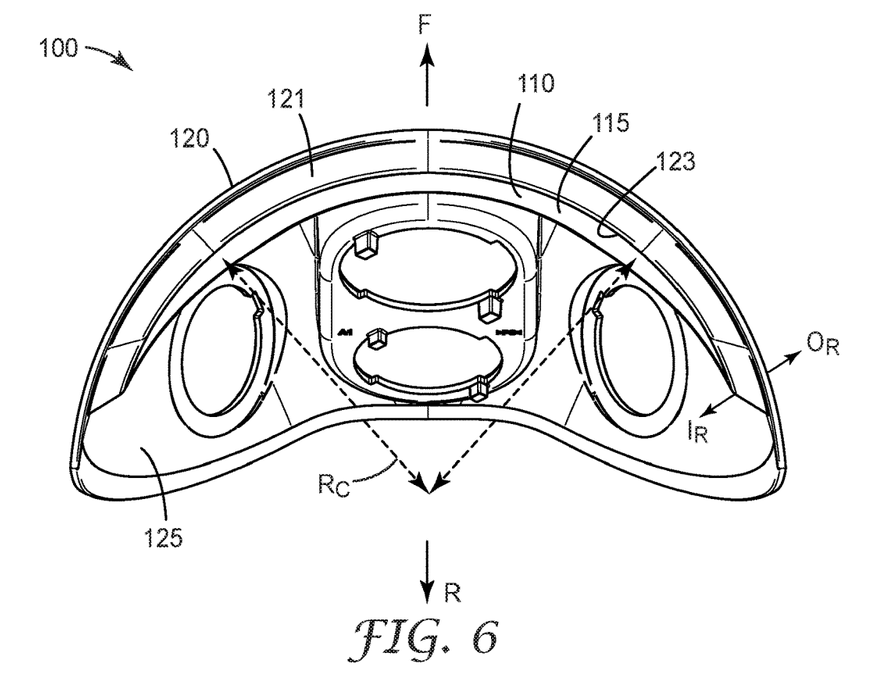
FIG. 6 is a top view of the exemplary facepiece of FIG. 4.

Although terms such as "first" and "second" may be used in this disclosure, it should be understood that those terms are used in their relative sense only unless otherwise noted. Terms such as "front", "rear", "forward", "rearward", "top", bottom", "upper", lower", "under", "over", "upward", "downward", and the like, have their customary meanings with reference to a respirator fitted onto a vertically upright head of a human wearer. Exemplary forward and rearward directions F and R are indicated in FIGS. 5 and 6.

Figure 4:
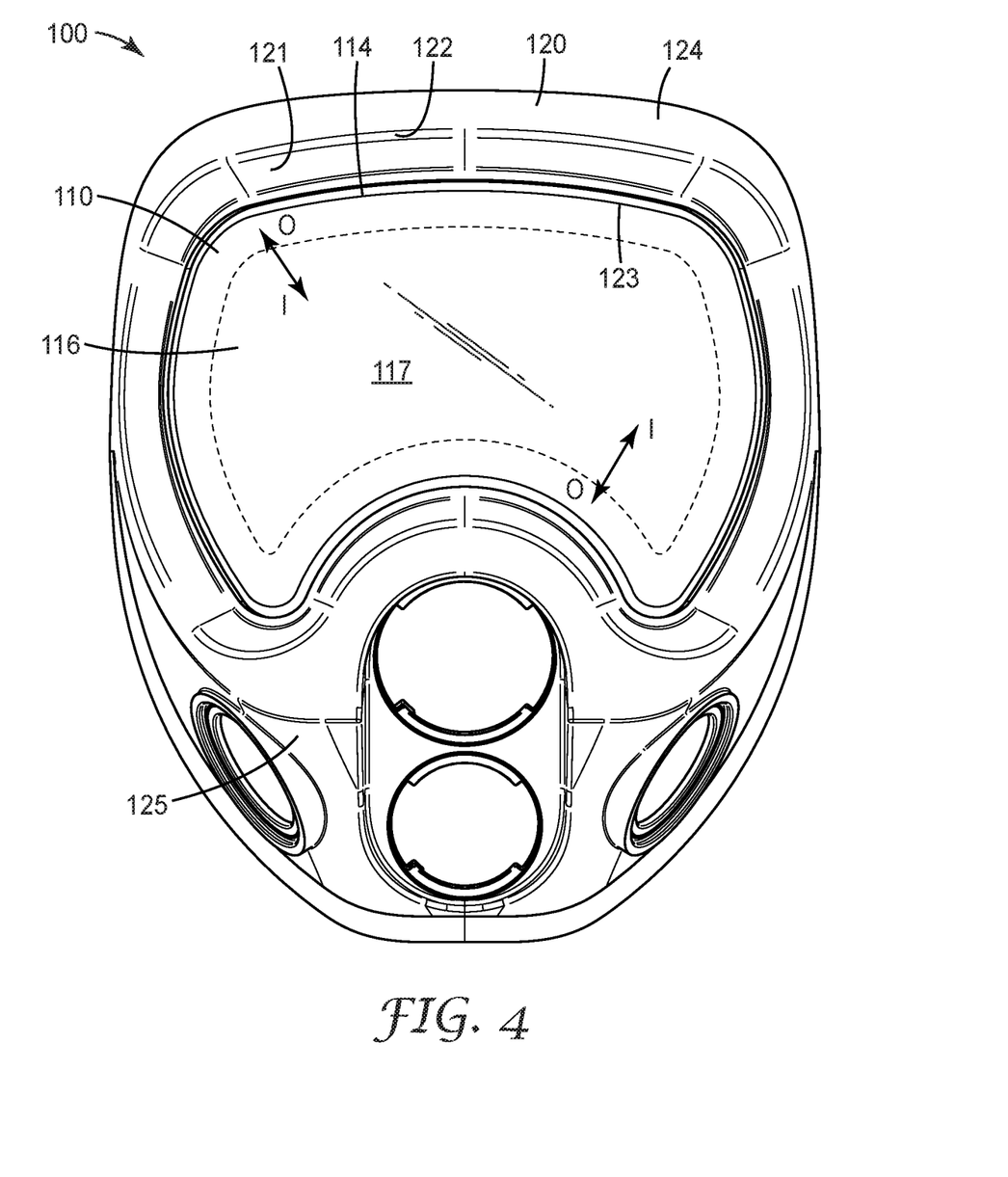
FIG. 4 is an isolated front view of an exemplary facepiece of a full-face respirator.

Terms such as "inward" and associated terminology are used herein with reference to a respirator facepiece and a lens thereof, and denote a direction that is toward a generally central area of the lens, along a path that that at least generally follows the local major plane of the lens. Terms such as "outward" and associated terminology denote a direction that is away from the central area of the lens, along a path that that at least generally follows the local major plane of the lens. A central area 117 (the area circumscribed by the dotted line) of a lens 110, and exemplary inward and outward directions I and O, are indicated in FIG. 4.

Terms such as "radially-inward" indicate directions generally toward the face of a wearer of the respirator; terms such as "radially-outward" indicate directions generally away from the face; that is, generally toward an outside environment that is viewed through a transparent lens of the respirator. The terms "radially-inward" and "radially-outward" are used in view of the curvature of the facepiece and lens and to distinguish from the above-recited "inward" and "outward" directions; however, the term "radially" does not require that the facepiece and/or the lens must necessarily exhibit a shape that follows a strictly circular (constant radius of curvature) arc. Exemplary radially-inward and radially-outward directions $I_R$ and $O_R$ are indicated in FIG. 6.

As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−10% for quantifiable properties). The term "essentially" means to a very high degree of approximation (e.g., within plus or minus 2% for quantifiable properties); it will be understood that the phrase "at least essentially" subsumes the specific case of an "exact" match. However, even an "exact" match, or any other characterization using terms such as e.g. same, equal, identical, uniform, constant, and the like, will be understood to be within the usual tolerances or measuring error applicable to the particular circumstance rather than requiring absolute precision or a perfect match. The term "configured to" and like terms is at least as restrictive as the term "adapted to", and requires actual design intention to perform the specified function rather than mere physical capability of performing such a function. All references herein to numerical parameters (dimensions, ratios, and so on) are understood to be calculable (unless otherwise noted) by the use of average values derived from a number of measurements of the parameter.

DETAILED DESCRIPTION

Figure 1:
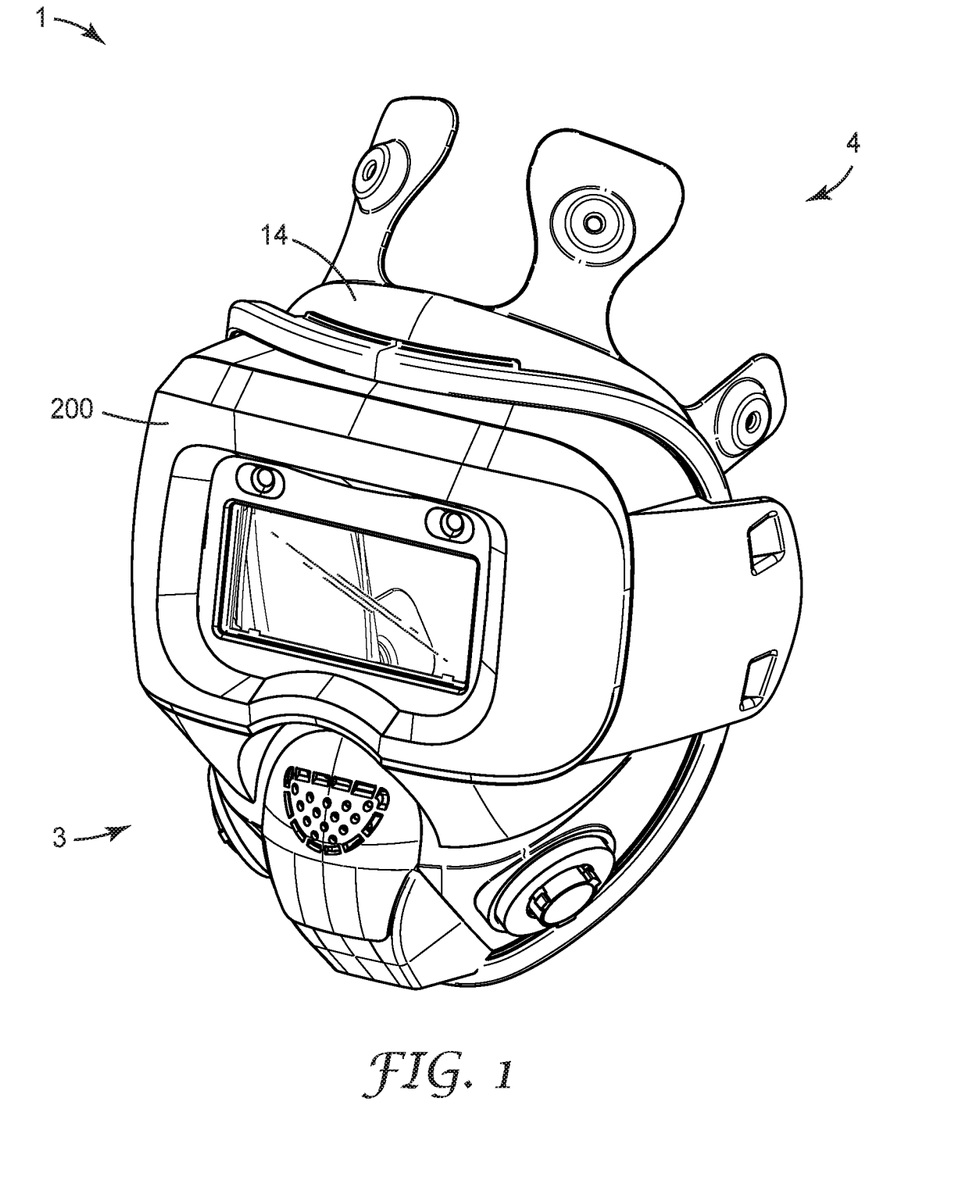
FIG. 1 is a perspective view of an exemplary full-face respirator with an exemplary vision-protecting module attached thereto.
Figure 2:
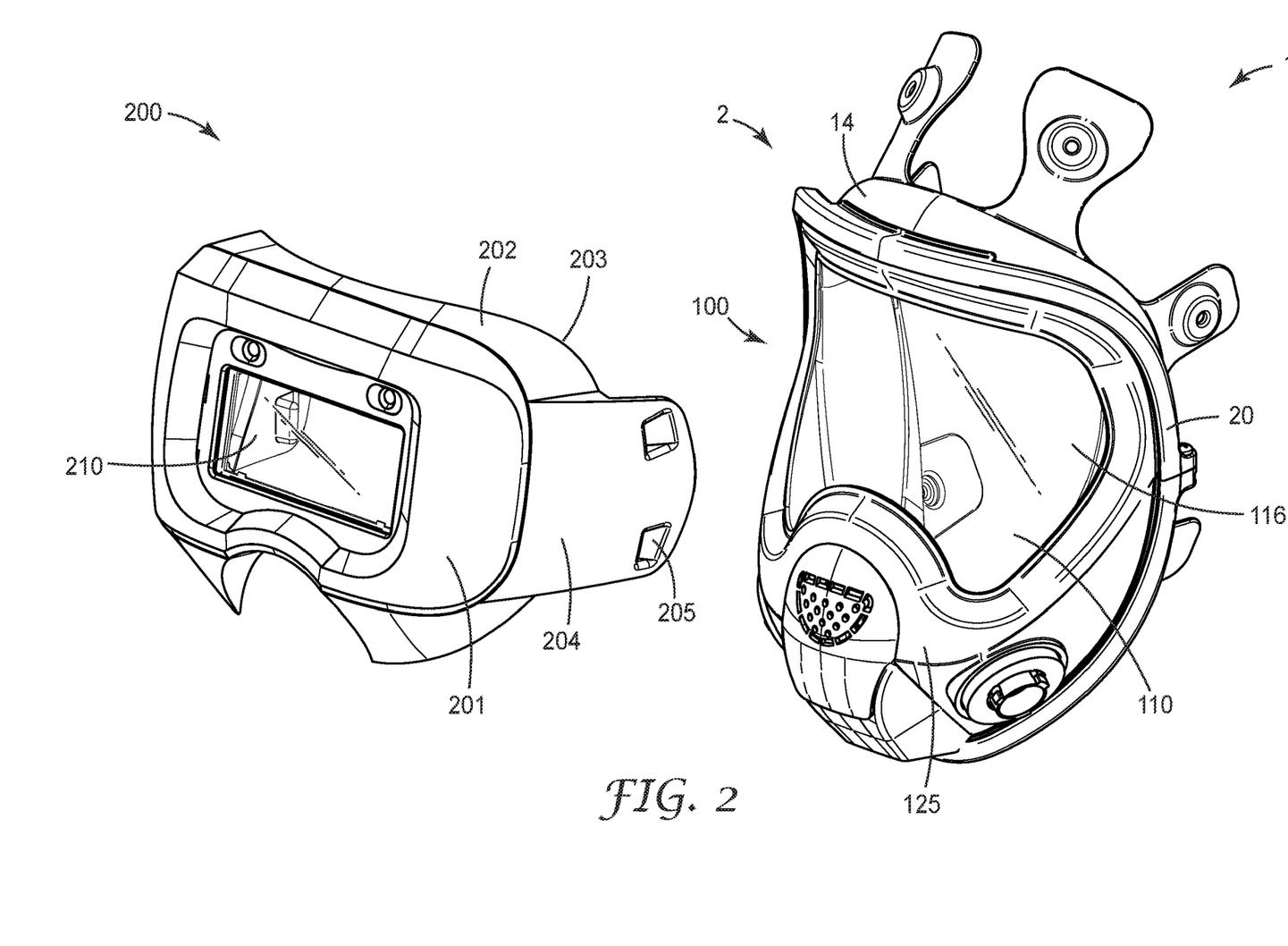
FIG. 2 is a perspective view of an exemplary full-face respirator with an exemplary vision-protecting module having been removed therefrom.

Disclosed herein is an exemplary full-face respirator that is configured to enable a vision-protecting module to be mounted thereto. FIG. 1 is a front-side perspective view of an exemplary full-face respirator 1 with a front side 3 and a rear side 4 and with an exemplary vision-protecting module 200 mounted on the a front side 4 thereof; FIG. 2 shows respirator 1 with vision-protecting module 200 detached therefrom. Exemplary respirator 1 includes a face seal 14, a facepiece 100, and a perimeter frame 20 that clamps facepiece 100 to face seal 14 to form a respirator body 2, as is apparent from the exploded perspective view of FIG. 3. A harness (not shown in any Figure) can be attached to respirator body 2 (e.g. to face seal 14, facepiece 100, and/or perimeter frame 20) for securing respirator 1 to a head of a wearer. Face seal 14 serves to conform to a users face and thus may be made of any suitably resilient and/or cushioning material.

Facepiece 100 functions in combination with face seal 14 to prevent unfiltered air from reaching a face of the wearer. That is, facepiece 100, face seal 14, and the wearer's face and head, combine to provide a sealed airspace that outside air can enter only by passing through one or more filters (which term broadly encompasses e.g. any fibrous web or webs, collection of particles, sorbents, and so on, which are configured to remove gases, vapors and/or particulate matter from a gaseous mixture). In some embodiments one or more such filters may be located on, e.g. attached to and supported by, respirator body 2 of respirator 1. Such filters may be located e.g. in a filter cartridge, canister, or the like, of any suitable design. In other embodiments one or more such filters may be in a remote location (e.g. belt-mounted) with clean and/or filtered air being supplied to the sealed airspace through a hose as motivated e.g. by a powered fan, air pump, air tank or air compressor. In some embodiments, a nose cup (not shown in any Figure) may be coupled to facepiece 100 and may be configured to surround a nose and mouth of the wearer and to direct filtered air thereto. As will be familiar to those with experience in the design of respiratory protection devices, respirator 1 may be outfitted with various components and accessories that facilitate operation of respirator 1. Such items may include e.g. one or more filter cartridges, inhalation valves, exhalation values, valve covers, speaking diaphragms, gaskets, and so on. To facilitate attachment of such items to respirator 1, facepiece 100 may comprise any number of fittings, apertures, ports connections, and the like, some of which are visible in various Figures herein. The functioning of such items and the manner in which they may be included and used in a respirator are well understood to those of skill in the art and will not be addressed herein. Respirators, including full-face respirators, and components and functioning thereof, are described e.g. in U.S. Pat. Nos. 7,594,510 and 8,839,788, which are incorporated by reference in their entirety herein.

As noted, respirator 1 comprises a facepiece 100. Facepiece 100 comprises a transparent lens 110. By a transparent lens of a facepiece is meant a sheet or pane (comprised of one or more layers of material) that is at least substantially or essentially transparent to visible light. A lens of a facepiece serves (in combination with other components of the respirator) to provide physical isolation of an airspace from the outside environment, to protect a wearer's face and eyes from physical hazards such as liquid splatters, particulate debris, to provide impact protection, and so on. In many embodiments, a lens 110 of a facepiece 100 may exhibit a generally arcuate (e.g. semi-cylindrical) shape in which lens 110 is curved about a generally vertical axis. In some embodiments a lens 110 may exhibit a relatively constant radius of curvature throughout the entirety of lens 110; i.e., it may exhibit a shape that is a section of a cylinder. In various embodiments, lens 110 may exhibit a thickness (in the radial inward-outward direction) of at least 0.5, 1.0, 1.5, or 2.0 mm; in further embodiments, lens 110 may exhibit a thickness of at most 5.0, 4.0, 3.0, or 2.5 mm.

Figure 3:
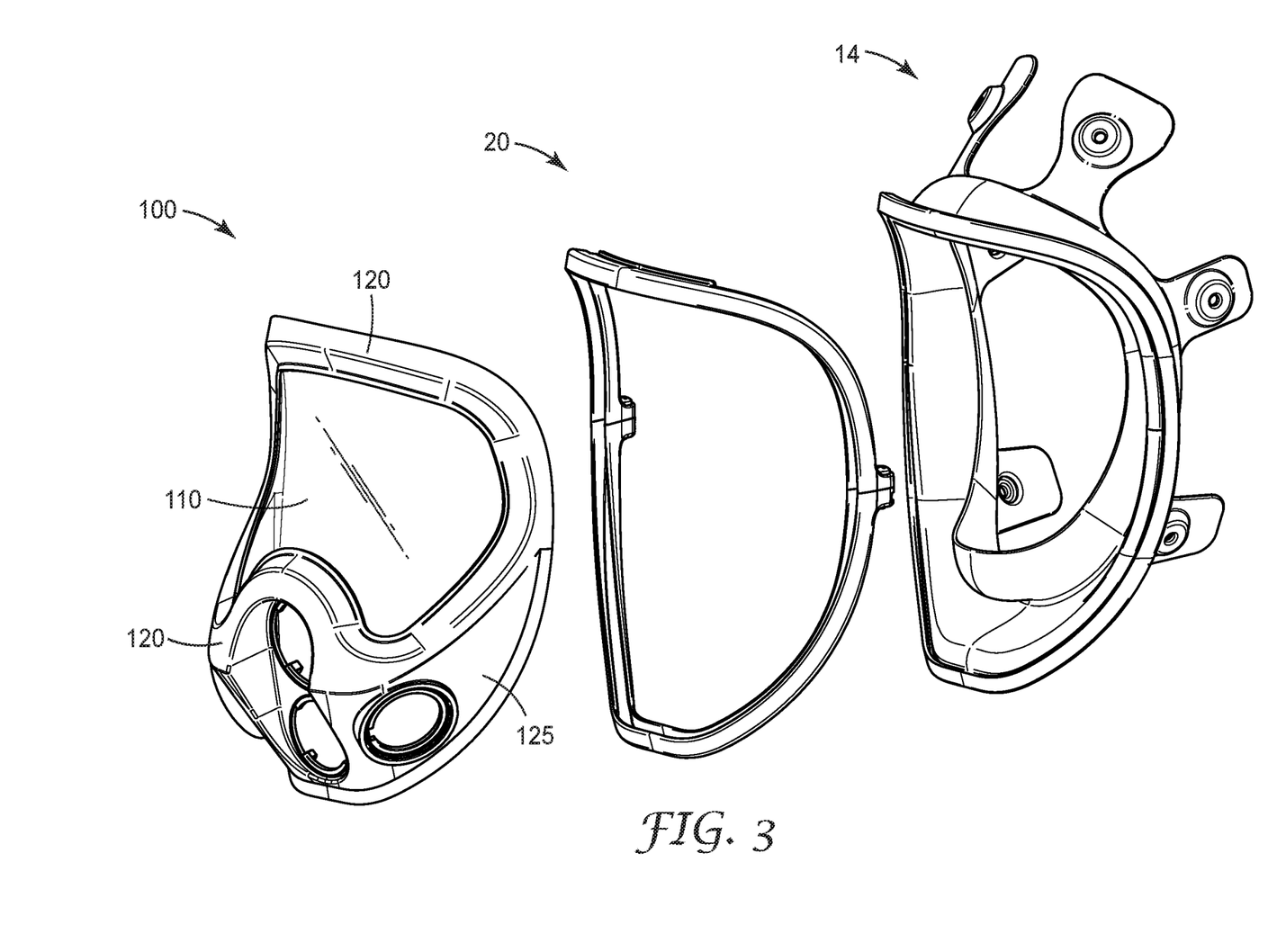
FIG. 3 is a perspective exploded view of an exemplary full-face respirator.

Facepiece 100 further comprises a chassis 125 as indicated e.g. in FIGS. 3 and 4. Chassis 125 is opaque, meaning that it admits substantially no visible light (noting that in actual use, various apertures and ports that are visible in chassis 125 as shown in FIG. 4 will be fitted with various items and components that will occlude them so that no visible light can penetrate therethrough in such manner as to reach the wearer's eyes). Opaque chassis 125 includes an opaque frame 120 that outwardly bounds (along the previously-mentioned inward-outward direction) transparent lens 110 as is clear e.g. from FIG. 4. In at least some embodiments, opaque frame 120 outwardly bounds the entirety of transparent lens 110. In many embodiments, opaque frame 120 will exhibit a generally arcuate shape in which frame 120 is curved about a generally vertical axis, e.g. in similar manner to lens 110. In at least some embodiments, opaque frame 120 of opaque chassis 125 will provide the radially-outwardmost locations of chassis 125 (disregarding any items such as e.g. filter cartridges and so on that may be attached to chassis 125). That is, in such embodiments the radially-outwardmost surface 124 of frame 120 will be the radially-outwardmost surface of facepiece 100.

Opaque frame 120 of opaque chassis 125 will be connected to the outward edge 114 of lens 110 by an opaque ramp 121. Specifically, as illustrated in FIG. 4, ramp 121 integrally extends inwardly from inward edge 122 of frame 120 of chassis 125, with inward edge 123 of ramp 121 being joined to outward edge 114 of lens 110. In some convenient embodiments chassis 125 may be a single, integral item, i.e. consisting of a single, uniform composition and formed in a single operation (e.g. a molding operation). In such cases ramp 121 and inward edge 123 thereof, and frame 120, will all be integral portions of chassis 125. (Such a requirement does not preclude the attachment of other items to chassis 125 in the manner noted above.)

Facepiece 100, including transparent lens 110 and opaque chassis 125 thereof, is by definition a unitary, inseparable piece. By this is meant that lens 110 and chassis 125 are portions of a facepiece that is not configured or intended to be separated into multiple pieces in ordinary use and/or servicing of respirator 1. In other words, lens 110 and chassis 125 are inseparable from each other, meaning that they cannot be separated from each other without being broken or otherwise unacceptably damaged. In many convenient embodiments, the inseparable joining of lens 110 and chassis 125 to each other may be performed by co-molding, overmolding, or any similar process, so that at least some surfaces of lens 110 (e.g. a surface of outward edge 114) and some surfaces of ramp 121 of chassis 125 (e.g. a surface of inward edge 123 of ramp 121) are melt-bonded to each other. To facilitate such bonding, in some embodiments both lens 110 and chassis 125 may be made of similar or identical materials, e.g. organic polymer molding resins that are chemically compatible and generally, substantially or essentially identical except for the presence of one or more opacifying agents in the resin that forms the chassis. In some convenient embodiments both lens 110 and chassis 125 are made of polycarbonate. In some embodiments lens 110 and chassis 125 may be made of materials that differ at least somewhat in composition, e.g. as long as the materials are still sufficiently melt-bondable to each other to permit the formation of an inseparable facepiece as disclosed herein.

If desired, some other method of joining ramp 121 of chassis 125 to lens 110 may be used, as long as it provides an inseparable bond. Such methods might include e.g. ultrasonic bonding, solvent welding, and so on. However formed, the bond will be inseparable and will provide a fluid-tight junction. It will be appreciated that the term "edge" as used above is used broadly and does not limit the manner in which an outward edge 114 of lens 110 is joined to an inward edge 123 of ramp 121. That is, such joining is not limited e.g. to a simple butt joint. Rather, for example, a portion of inward edge 123 of ramp 121 may overlap a portion of outward edge 114 of lens 110; or, portions of inward edge 123 of ramp 121 may sandwich portions of outward edge 114 of lens 110, and so on.

Full-face respirator 1 as disclosed herein is configured to receive a vision-protecting module 200 in a manner shown in exemplary embodiment in FIGS. 1 and 2. By a vision-protecting module is meant a device comprising an opaque housing 201 that supports a vision-protecting lens 210, as shown in exemplary embodiment in FIG. 2. By a vision-protecting lens is meant a lens that is configured to protect a wearer's eyes from at least high-intensity visible light (as well as non-visible radiation such as e.g. ultraviolet radiation) that may arise in operations such as welding, soldering, brazing, laser-cutting, laser-engraving, and the like. Vision-protecting lens 210 of vision-protecting module 200 is thus distinguished from lens 110 of facepiece 100 (noting that lens 110 provides physical protection and that while it may be e.g. tinted slightly if desired, it does not provide protection against high-intensity visible light in the manner of vision-protecting lens 210).

In some embodiments lens 210 may be a passive (e.g. unpowered) lens that exhibits a permanent, unchangeable "dark" state. Such a state may be characterized by a Shade Number; in various embodiments lens 210 may comprise a Shade Number of at least 4, 6, 8, 10, or 12. In some embodiments, lens 210 may comprise an automatic darkening filter that includes a switchable shutter that is capable of controllably blocking at least visible light. For example, such a shutter can be reversibly switched between at least a light state (e.g. in which is it relatively highly light-transmissive) and a dark state (e.g. in which it is relatively non-transmissive to light). Such a switchable shutter may comprise e.g. one or more liquid crystal layers, polarizing filters, electrochromic materials, etc., as are familiar to those of ordinary skill. Such a device may comprise any items, components or the like (e.g. light sensors, signal processors, switches, power sources, and so on) as needed for functioning of the device.

Vision-protecting module 200 may be mounted on the front of respirator 1 and attached to respirator body 2 in any suitable manner. In some embodiments, module 200 may comprise at least one latch 205 that is provided on a side member 204 of module 200 and that can be latched to a portion of component of respirator body 2 in any suitable manner. Such a latch may be of any suitable design and may be securable e.g. to perimeter frame 20 and/or to facepiece 100 or to a complementary latch that is provided on perimeter frame 20, facepiece 100 and/or on face seal 14. However configured, any such system of one or more latches, connectors, fasteners, bands, snaps, clasps, or the like, will allow module 200 to be installed on respirator 1 (and to be removed therefrom) manually, by a wearer of respirator 1, without requiring the use of any special tools, fixtures or equipment.

Vision-protecting module 200 will be mounted on respirator 1, and attached to respirator body 2 thereof, so that no unacceptable light leaks are present between module 200 and respirator body 2. To achieve this, a rear edge 203 of opaque skirt 202 of opaque housing 201 of module 200 may be abutted against a surface of an opaque portion of facepiece 100. Thus for example, rear edge 203 of skirt 202 may be abutted against a portion of opaque frame 120 (e.g. at or near inward edge 122 of frame 120). Or, rear edge 203 may be abutted against a portion of opaque ramp 121, or against some portion of an inward edge 123 of ramp 121. Combinations of any of these are possible. Thus in some embodiments, some sections of rear edge 203 may be abutted against a portion of frame 120 with other sections of rear edge 203 being abutted against a portion of ramp 121 or edge 123 thereof. Whichever of these sections are to be contacted by rear edge 203, they collectively form an opaque, light-sealing area that will be shaped and sized so that it is congruent with the shape and size of rear edge 203 of opaque skirt 202 of opaque housing 201 of module 200. Such an opaque, light-sealing area can provide that no unacceptable light leaks are present. In some embodiments, side members 204 of module 200 may be opaque and may further assist in minimizing any light leaks. In some embodiments, at least a portion of rear edge 203 of opaque skirt 202 of opaque housing 201 of module 200 may be abutted against a surface of an opaque portion of a perimeter frame 20 of the type described earlier herein. It will be appreciated that such a perimeter frame 20 is a separate component that is configured to couple a facepiece 100 to a face seal 14, and is thus distinguished from an opaque frame 120 of a facepiece 100. This is true even if, for example, a portion, or all of, the perimeter frame 20 is opaque.

Figure 7:
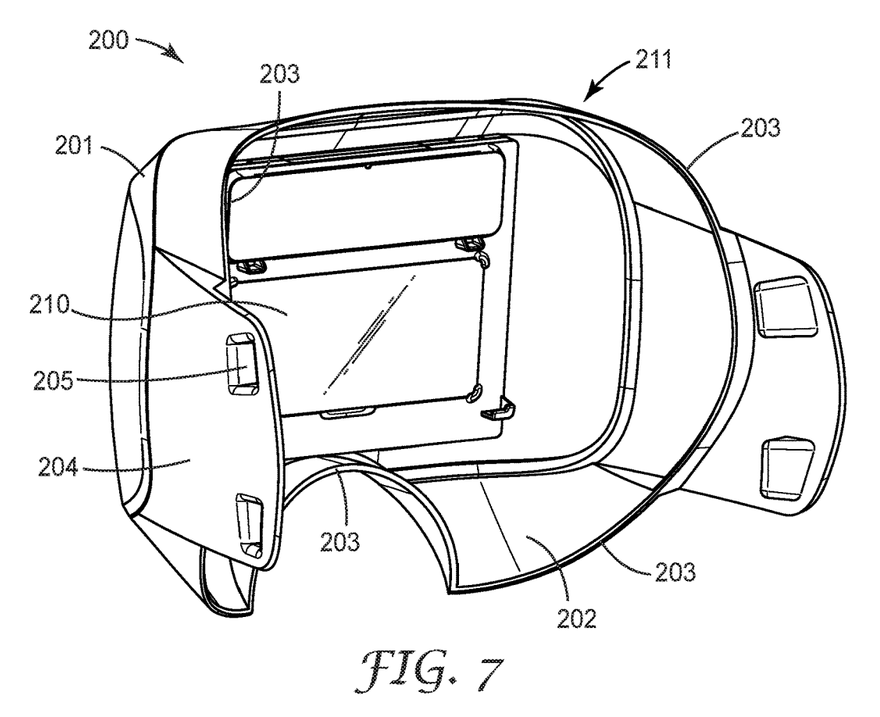
FIG. 7 is a side-rear perspective view of an exemplary vision-protecting module for a full-face respirator.

In some embodiments, vision-protecting lens 210 of vision-protecting module 200 may be movable relative to housing 201 of module 200 so that lens 210 can be moved to provide an increased field of view without having to remove module 200 from respirator 1. Thus in some embodiments, lens 210 may be connected to housing 201 by at least one connection (indicated generally at 211) that allows the desired movement. In various embodiments, such a connection may be a hinged connection, and/or may be extendable and/or jointed. A connection of this general type can allow lens 210 to be moved from a first, vision-protecting position (e.g. as shown in FIG. 7) to a second, non-vision-protecting position. In specific embodiments the movement of lens 210 from the first position toward the second position may include upward movement, forward movement, rotation from a vertical orientation toward a horizontal orientation, or any combination of these, whether sequential or simultaneous.

Figure 8:
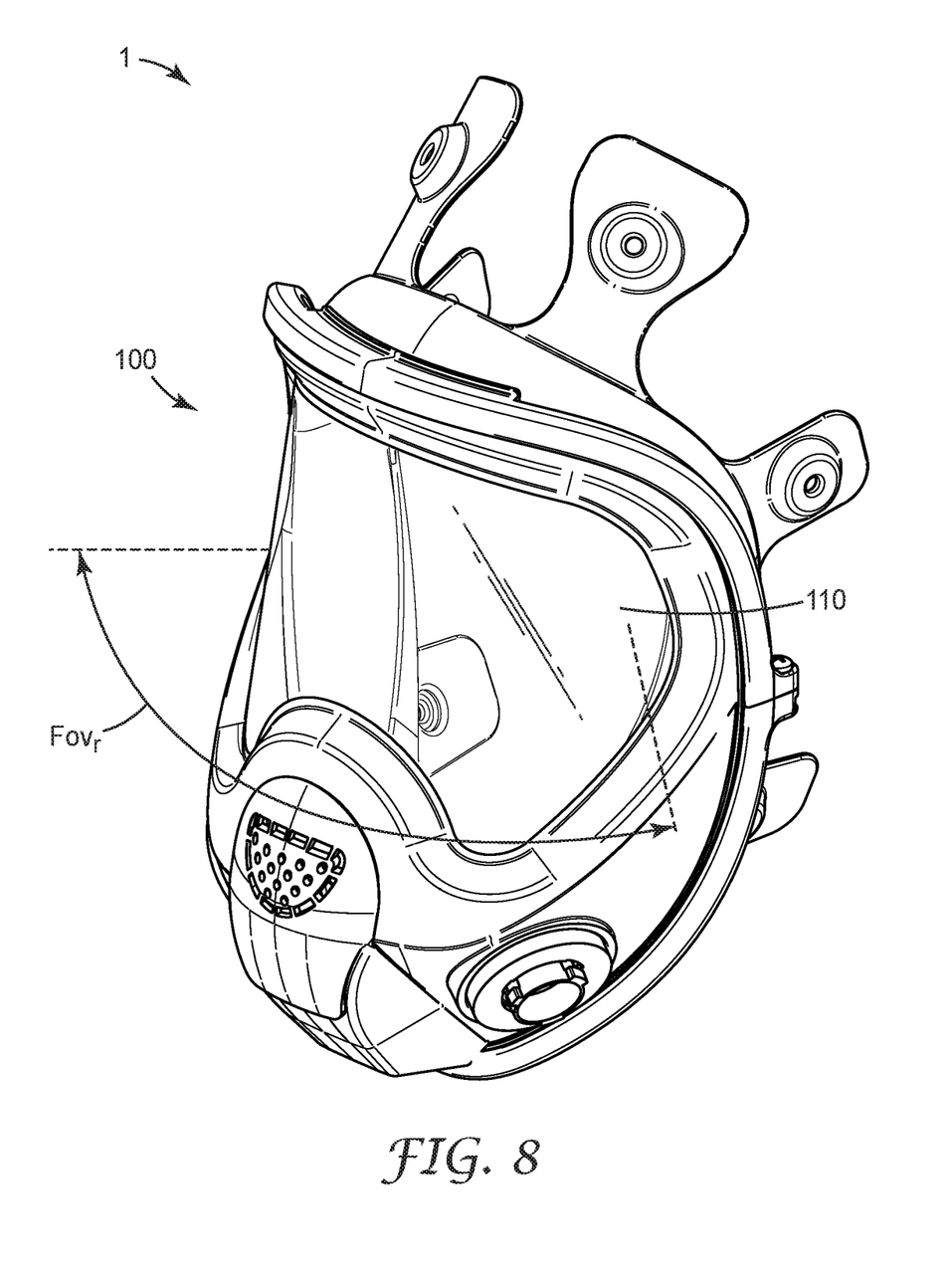
FIG. 8 is a perspective view showing a field of view of an exemplary full-face respirator without a vision-protecting module mounted thereon.

In the design and use of full-face respirators, providing the wearer with a wide field of view is desirable. It is particularly desirable to provide a field of view that is relatively wide in the lateral directions (that is, to the left and right of the wearer), as will be appreciated in consideration of the lateral field of view ($fov_r$) of full-face respirator 1 as depicted in generic representation in FIG. 8.

Figure 9:
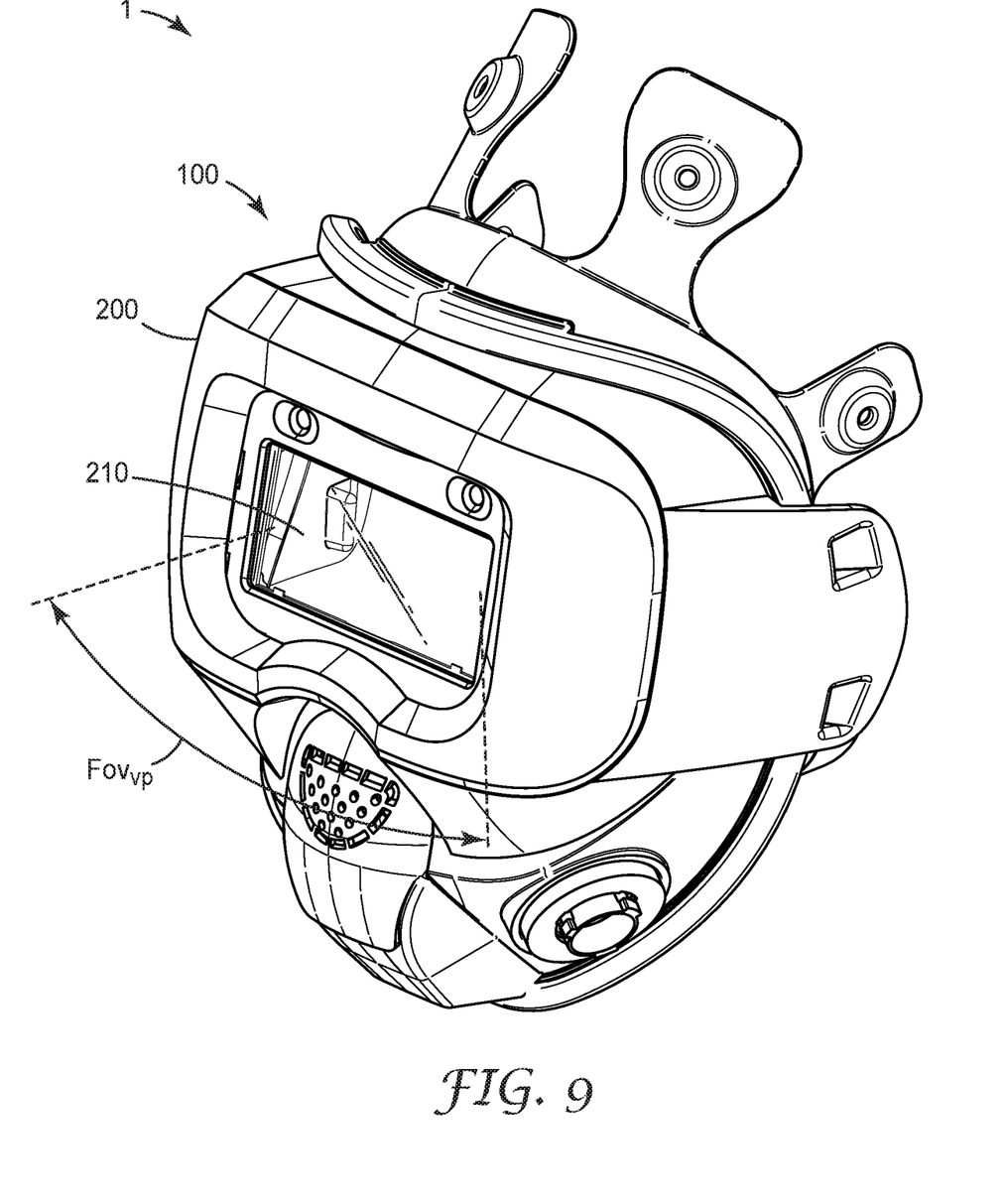
FIG. 9 is a perspective view showing a field of view of an exemplary full-face respirator with a vision-protecting module mounted thereon.

Full-face respirator 1 as disclosed herein is configured so that a vision-protecting module 200 can be mounted on the front of facepiece 100 of respirator 1 as described above. Mounting a vision-protecting module on the front of a full-face respirator can significantly reduce the field of view, particularly in the lateral directions. The arrangements disclosed herein allow a vision-protecting module to be mounted on a full-face respirator so that a relatively wide field of view through the vision-protecting lens of the vision-protecting module is achieved. In brief, this can be achieved by recessing at least a portion of lens 110 of facepiece 100 in a radially-inward direction. This enables a vision-protecting lens 210 of a vision-protecting module 200 to be positioned further rearward (i.e., closer to the eyes of the wearer of the respirator) so that a wider field of view through the vision-protecting lens 210 is obtained. Thus, as shown in generic representation in FIG. 9, respirator 1 and vision-protecting module 200 can be configured according to the disclosures herein, to provide a relatively wide lateral field of view through lens 210 of vision-protecting module 200 (fov$_{vp}$), as depicted in generic representation in FIG. 9.

The ability to position vision-protecting lens 210 further rearward, as made possible by recessing lens 110 of facepiece 100 radially-inward, may be of particular importance when vision-protecting lens 210 comprises an automatic darkening filter. This is because automatic darkening filters are often rather thick (as evident from inspection of FIG. 7) due to the multiple layers involved. In fact, automatic darkening filters are often supplied as a cartridge (e.g. of the general type described in U.S. Pat. No. 9,861,530) that comprises a power source, hardware, operating circuitry, etc. in addition to the actual layers that perform the filtering, all of which adds to the bulk of the item as installed in a vision-protection module. Thus, the present arrangements can enable a relatively wide field of view even when vision-protecting module 200 includes an automatic darkening filter. Still further, the ability to position vision-protecting lens 210 further rearward can allow the overall size (in particular the forward-rearward depth) of vision-protecting module 200 to be minimized. This can provide that a full-face respirator 1 with a vision-protecting module 200 installed on the front side thereof may be more easily used in confined spaces.

The field of view of a full-face respirator can be evaluated quantitatively by using the procedures outlined in EN 136: 1998 as specified in 1998, which is incorporated by reference herein in its entirety. Such evaluations provide a Field of View (FOV) parameter that can best be understood as generally corresponding to a percentage of the field of view available to the eyes of a human being unencumbered by a respirator, and will not exceed 100%.

In various embodiments, a full-face respirator 1 as disclosed herein may exhibit a Field of View, through lens 110 in the absence of a vision-protecting module, of at least 70, 75, 80, or 85 percent. In some embodiments, such a respirator 1 with a vision-protecting module 200 mounted thereon with the vision-protecting lens 210 thereof in a first, vision-protecting position, may exhibit a Field of View of at least 12, 13, 14, 15, 16, 17, 18, 19, 20, 21 or 22 percent. In further embodiments, a respirator 1 with a vision-protecting module 200 mounted thereon with the vision-protecting lens 210 thereof in a first, vision-protecting position, may exhibit a Field of View of at most 30, 29, 28, 27, 26, 25, 24, 23, 22, 21 or 20 percent. In further embodiments, such a respirator 1 with a vision-protecting module 200 mounted thereon but with a vision-protecting lens 210 of module 200 having been moved to a second, non-vision-protecting position, may exhibit a Field of View of at least 30, 35, 40, or 45 percent.

To enable the arrangements disclosed above, at least a portion of lens 110 of facepiece 100 is recessed radially-inwardly. The terminology of recessed radially-inwardly refers to the relationship of radially-outermost surface 116 of transparent lens 110 to radially-outwardmost surface 124 of opaque frame 120 of chassis 125. Thus as shown in exemplary embodiment in FIG. 5, radially-outwardmost surface 116 of lens 110 will be recessed radially-inward a distance $D_R$ relative to radially-outwardmost surface 124 of frame 120. In various embodiments, distance $D_R$ may be at least 3, 4, 5, 6, 7, 8, 9 or 10 mm. In further embodiments, a distance $D_R$ may be at most 15, 12, 10, 9, 8, 7 or 6 mm. In various embodiments, at least 5, 10, 20, 40, 60, 70, 80, 90, or 98 percent, or the entirety, of the total area of lens 110 (measured on its outside surface) may be recessed a distance $D_R$. In some embodiments (e.g. in which lens 110 is in the shape of a cylindrical section, e.g. with a constant radius of curvature), distance $D_R$ may be at least generally, substantially or essentially constant over the entire area of lens 110.

Distance of recession $D_R$ can be considered in relation to the radius of curvature $R_c$ of lens 110. Such a radius of curvature $R_c$ (drawn from radially-inward surface 115 of lens 110) is depicted in exemplary embodiment in FIG. 6, which is a top view looking downward generally along the vertical axis of facepiece 100. In various embodiments, the ratio of the distance of recession $D_R$ of lens 110 to the radius of curvature $R_c$ of lens 110, can be at least 3, 4, 5, 6, 7, 8 or 9 percent. In further embodiments, such as ratio can be at most 12, 11, 10, 9, 8, 7 or 6 percent. By way of a specific example, a recession distance $D_R$ of 5 mm and a radius of curvature $R_c$ of 90 mm would provide a ratio of approximately 5.6 percent. If the radius of curvature of the lens 110 is variable, the local radius of curvature at a particular location of lens 110 can be used for calculating this distance ratio at that location. In various embodiments, at least 5, 10, 20, 40, 60, 70, 80, 90, or 98 percent, or the entirety, of the total area of lens 110 may be recessed so as to exhibit such a ratio.

Distance of recession $D_R$ can be considered in relation to the thickness (in the radially inward-outward direction) of lens 110. In various embodiments, the ratio of the distance of recession $D_R$ of lens 110 to the thickness of lens 110, can be at least 1.5, 2, 2.5, 3, 4, or 5. In further embodiments, such as ratio can be at most 10, 9, 8, 7, 6, 5, or 4. By way of a specific example, a recession distance $D_R$ of 5 mm and a lens thickness of 2.0 mm would provide a ratio of approximately 2.5. If the thickness of lens 110 is variable, the local thickness at a particular location of lens 110 can be used for calculating this ratio at that location. In various embodiments, at least 5, 10, 20, 40, 60, 70, 80, 90, or 98 percent, or the entirety, of the total area of lens 110 may be recessed so as to exhibit such a ratio.

The recessing of lens 110 relative to frame 120 of chassis 125 may be achieved by appropriately configuring the above-described opaque ramp 121 that connects opaque frame 120 to the outward edge 114 of transparent lens 110. Specifically, ramp 121 will extend from inward edge 122 of frame 120 in a direction that is not only inward (toward generally central area 117 of lens 110) as mentioned previously. Rather, ramp 121 will also extend radially-inwardly (i.e., it will incline toward the face of a wearer of the respirator), e.g. in the manner of ramp 121 of FIG. 5. Thus, the aforementioned inward edge 123 of ramp 121 is also a radially-inward edge of ramp 123. In various embodiments, ramp 121 can extend from inward edge 122 of frame 120 of chassis 125 to outward edge 114 of lens 110, along a direction that is at a local angle with respect to lens 110, of from at least 20, 30 or 40 degrees, to at most 70, 60 or 50 degrees. By way of a specific example, exemplary ramp 121 as depicted in FIG. 5 appears to extend at an angle that is in the range of 40-50 degrees with respect to lens 110.

As noted previously herein, frame 120, and lens 110 at least a portion of which is radially-inwardly recessed relative to frame 120, are portions of unitary, inseparable facepiece 100. The recessing of one portion of a unitary, inseparable facepiece relative to another portion of that same unitary, inseparable facepiece, will be distinguished from a case in which a lens (or a facepiece) is installed in or coupled to a separate structure (e.g. a hardhat, welding helmet, welding shield, a face seal, a perimeter frame that is used to attach a facepiece to a face seal, and so on) in such a manner that the lens (or facepiece) is recessed relative to a portion (e.g. a brow) of the separate structure. It will be appreciated that an arrangement of the latter type will not necessarily enable a vision-protecting module to be advantageously positioned rearwardly inwardly closer to a facepiece in the manner disclosed herein. Thus in summary, an arrangement in which at least a portion of a transparent lens is recessed relative to a radially-outwardmost surface of an opaque frame of a chassis of a facepiece as disclosed herein, will be distinguished from an arrangement in which a transparent lens is not recessed relative to an opaque frame of a chassis of a facepiece (even though the lens might be recessed relative to some other component of the respirator, e.g. a perimeter frame). Arrangements in which a transparent lens is not recessed relative to a radially-outwardmost surface of an opaque frame of a chassis of a facepiece in the manner disclosed herein, include for example those presented in the Figures of U.S. Pat. Nos. 7,594,510 and 8,839,788.

It will be appreciated that the arrangements disclosed herein can allow facepieces with recessed lenses as disclosed herein, and conventional facepieces without recessed lenses, to share a common chassis size and shape. This can allow the use of standardized face seal sizes and shapes (e.g. "universal" face seals) that can accommodate conventional facepieces and can also accommodate facepieces that have radially-inwardly-recessed lenses. This can simplify the manufacture of multiple product lines (e.g. "generic" full-face respirators, and full-face respirators that are specially configured to accept a vision-protection module).

LIST OF EXEMPLAR EMBODIMENTS

Embodiment 1 is a full-face respirator comprising: a face seal; and, a facepiece comprising a transparent lens and an opaque chassis that includes an opaque frame that outwardly bounds the lens, the facepiece being secured to the face seal to form a respirator body of the full-face respirator, wherein at least 70 percent of a total area of the lens is recessed radially-inwardly relative to the opaque frame of the opaque chassis, a distance that is from 4 percent to 10 percent of a radius of curvature of the lens.

Embodiment 2 is the full-face respirator of embodiment 1 wherein the respirator is configured to receive a vision-protecting module that is configured to be mounted on a front side of the respirator body and attached to the respirator body with a rear edge of an opaque skirt of an opaque housing of the vision-protecting module abutted against an opaque portion of the opaque chassis of the facepiece.

Embodiment 3 is the full-face respirator of any of embodiments 1-2 wherein the transparent lens of the facepiece is connected to the opaque chassis of the facepiece by an opaque ramp that integrally extends inwardly and radially-inwardly from an inward edge of the chassis; and, wherein an inward edge of the opaque ramp is non-separably joined to, and outwardly bounds, an outward edge of the transparent lens.

Embodiment 4 is the full-face respirator of embodiment 3 wherein the inward edge of the opaque ramp is melt-bonded to the outward edge of the transparent lens.

Embodiment 5 is the full-face respirator of any of embodiments 3-4 wherein the facepiece is an overmolded structure in which the opaque chassis and the opaque ramp integrally extending therefrom are overmolded onto the transparent lens.

Embodiment 6 is the full-face respirator of any of embodiments 3-5 wherein the opaque ramp extends inwardly and radially-inwardly from the inward edge of the chassis, at an angle of from 30 to 60 degrees relative to the transparent lens.

Embodiment 7 is the full-face respirator of any of embodiments 1-6 wherein at least 90 percent of the total area of the transparent lens is radially-inwardly recessed relative to the opaque frame.

Embodiment 8 is the full-face respirator of any of embodiments 1-6 wherein the entirety of the total area of the transparent lens is radially-inwardly recessed relative to the opaque frame.

Embodiment 9 is the full-face respirator of any of embodiments 1-8 further comprising a harness attached to the respirator body.

Embodiment 10 is the full-face respirator of any of embodiments 1-9 comprising a vision-protecting module mounted on a front side of the respirator body and detachably attached to the respirator body.

Embodiment 11 is the full-face respirator of embodiment 10 wherein when the vision-protecting module is mounted on a front side of the respirator body and detachably attached to the respirator body, a rear edge of an opaque skirt of an opaque housing of the vision-protecting module is abutted against an opaque portion of the opaque chassis of the facepiece.

Embodiment 12 is the full-face respirator of any of embodiments 10-11 wherein the vision-protection module is detachably attached to the respirator body by at least one latch that latches the opaque housing of the vision-protecting module to the respirator body.

Embodiment 13 is the full-face respirator of any of embodiments 11-12 wherein the opaque portion of the chassis against which the rear edge of the opaque skirt of the housing is abutted, is an opaque, light-sealing area of the chassis, which light-sealing area outwardly bounds the entirety of transparent lens and is shaped and sized so that it is congruent with a shape and size of the rear edge of the opaque skirt of the housing.

Embodiment 14 is the full-face respirator of embodiment 13 wherein the opaque, light-sealing area of the chassis is provided by portions of the opaque frame of the chassis, by portions of the opaque ramp of the chassis, or by portions of the opaque and the opaque ramp in combination.

Embodiment 15 is the full-face respirator of any of embodiments 10-14 wherein the full-face respirator exhibits a Field of View of at least 75 percent when the vision-protecting module is not present on the front side of the respirator body, and wherein the full-face respirator exhibits a Field of View of at least 16 percent when the vision-protecting module is mounted on the front side of the respirator body with a vision-protecting lens of the vision-protecting module in a vision-protecting position.

Embodiment 16 is the full-face respirator of any of embodiments 10-15 wherein the vision-protecting module comprises a vision-protecting lens that is movable back and forth between a first, vision-protecting position and a second, non-vision-protecting position, without removing the vision-protecting module from the respirator body.

Embodiment 17 is the full-face respirator of embodiment 16 wherein the vision-protecting lens of the vision-protecting module is movable relative to a housing of the vision-protecting module, between the first, vision-protecting position and the second, non-vision-protecting position.

Embodiment 18 is the full-face respirator of embodiment 17 wherein the vision-protecting lens of the vision-protecting module is connected to the housing of the vision-protecting module by a connection that is configured to allow the vision-protecting lens to be forwardly, upwardly and rotatably moved relative to the housing, from the first, vision-protecting position to the second, non-vision-protecting position.

Embodiment 19 is the full-face respirator of embodiment 16 wherein when the vision-protecting module is mounted on the front side of the respirator body with the vision-protecting lens in the second, non-vision-protecting position, the full-face respirator exhibits a Field of View of at least 35 percent.

Embodiment 20 is a full-face respirator comprising: a face seal; and, a facepiece comprising a transparent lens and an opaque chassis that includes an opaque frame that outwardly bounds the lens, the facepiece being secured to the face seal to form a respirator body of the full-face respirator, wherein at least 70 percent of a total area of the lens is recessed radially-inwardly relative to the opaque frame of the opaque chassis, a distance that is from 3.0 mm to 9.0 mm. Embodiment 21 is the full-face respirator of embodiment 20, comprising the features of any of embodiments 1-19.

Embodiment 22 is a full-face respirator comprising: a face seal; and, a facepiece comprising a transparent lens and an opaque chassis that includes an opaque frame that outwardly bounds the lens, the facepiece being secured to the face seal to form a respirator body of the full-face respirator, wherein at least 70 percent of a total area of the lens is recessed radially-inwardly relative to the opaque frame of the opaque chassis, a distance that is from 1.5 to 5.0 times a thickness of the lens. Embodiment 23 is the full-face respirator of embodiment 22, comprising the features of any of embodiments 1-19.

Embodiment 24 is a method of adapting a full-face respirator for use in a vision-protecting mode, the method comprising: mounting a vision-protecting module on a front side of a respirator body of the respirator of any of embodiments 1-23 and detachably attaching the vision-protecting module to the respirator body.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired.

Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). Although various theories and possible mechanisms may have been discussed herein, in no event should such discussions serve to limit the claimable subject matter. To the extent that there is any conflict or discrepancy between this specification as written and the disclosure in any document that is incorporated by reference herein but to which no priority is claimed, this specification as written will control.

What is claimed is:

1. A full-face respirator comprising:
    a resilient face seal configured to conform to a face of a user of the full-face respirator, the resilient face seal comprising multiple harness attachment elements;
    a facepiece comprising a transparent lens and an opaque chassis that includes an opaque frame that outwardly bounds the lens, the facepiece being secured to the face seal by a perimeter frame to form a respirator body of the full-face respirator and the facepiece, transparent lens, and opaque chassis being a unitary, inseparable entity,
        wherein at least 70 percent of a total area of the lens is recessed radially-inwardly relative to the opaque frame of the opaque chassis, a distance that is from 4 percent to 10 percent of a radius of curvature of the lens;
        wherein the transparent lens of the facepiece is connected to the opaque chassis of the facepiece by an opaque ramp that integrally extends inwardly and radially-inwardly from an inward edge of the chassis, an inward edge of the opaque ramp being non-separably joined, by melt-bonding, to an outward edge of the transparent lens;
        and wherein the facepiece is an overmolded structure in which the opaque chassis and the opaque ramp integrally extending therefrom are overmolded onto the transparent lens;
    and,
    a vision-protecting module mounted on a front side of the respirator body and detachably attached to the respirator body so that a rear edge of an opaque skirt of an opaque housing of the vision-protecting module is abutted against an opaque portion of the opaque chassis of the facepiece,
        wherein the opaque portion of the chassis against which the rear edge of the opaque skirt of the housing is abutted, is an opaque, light-sealing area of the chassis that is provided at least in part by portions of the opaque ramp of the chassis, the opaque, light-sealing area outwardly bounding the entirety of the transparent lens and being shaped and sized so that it is congruent with a shape and size of the rear edge of the opaque skirt of the housing.

2. The full-face respirator of claim 1 wherein the opaque ramp extends inwardly and radially-inwardly from the inward edge of the chassis, at an angle of from 30 to 60 degrees relative to the transparent lens.

3. The full-face respirator of claim 1 wherein at least 90 percent of the total area of the transparent lens is radially-inwardly recessed relative to the opaque frame.

4. The full-face respirator of claim 1 wherein the entirety of the total area of the transparent lens is radially-inwardly recessed relative to the opaque frame.

5. The full-face respirator of claim 1 further comprising a harness attached to the respirator body.

6. The full-face respirator of claim 1 wherein the full-face respirator exhibits a field of view (FOV) parameter of at least 75 percent when the vision-protecting module is not present on the front side of the respirator body, and wherein the full-face respirator exhibits a field of view (FOV) parameter of at least 16 percent when the vision-protecting module is mounted on the front side of the respirator body with a vision-protecting lens of the vision-protecting module in a vision-protecting position.

7. The full-face respirator of claim 1 wherein the vision-protecting module comprises a vision-protecting lens that is movable back and forth between a first, vision-protecting position and a second, non-vision-protecting position, without removing the vision-protecting module from the respirator body.

8. The full-face respirator of claim 7 wherein the vision-protecting lens of the vision-protecting module is movable relative to the housing of the vision-protecting module, between the first, vision-protecting position and the second, non-vision-protecting position.

9. The full-face respirator of claim 8 wherein the vision-protecting lens of the vision-protecting module is connected to the housing of the vision-protecting module by a connection that is configured to allow the vision-protecting lens to be forwardly, upwardly and rotatably moved relative to the housing, from the first, vision-protecting position to the second, non-vision-protecting position.

10. The full-face respirator of claim 7 wherein when the vision-protecting module is mounted on the front side of the respirator body with the vision-protecting lens in the second, non-vision-protecting position, the full-face respirator exhibits a field of view (FOV) parameter of at least 35 percent.

* * * * *